US009446119B2

(12) United States Patent
Poland et al.

(10) Patent No.: US 9,446,119 B2
(45) Date of Patent: Sep. 20, 2016

(54) VACCINIA VIRUS POLYPEPTIDES

(75) Inventors: Gregory A. Poland, Rochester, MN (US); Richard B. Kennedy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/593,365

(22) Filed: Aug. 23, 2012

(65) Prior Publication Data

US 2014/0050752 A1     Feb. 20, 2014

Related U.S. Application Data

(60) Provisional application No. 61/529,739, filed on Aug. 31, 2011.

(51) Int. Cl.
| | |
|---|---|
| A61K 39/285 | (2006.01) |
| A61K 38/00 | (2006.01) |
| A61K 39/295 | (2006.01) |
| C12N 7/00 | (2006.01) |
| C12N 15/86 | (2006.01) |
| A61K 39/12 | (2006.01) |
| C07K 14/005 | (2006.01) |

(52) U.S. Cl.
CPC ........... *A61K 39/285* (2013.01); *A61K 38/00* (2013.01); *A61K 39/12* (2013.01); *A61K 39/295* (2013.01); *C07K 14/005* (2013.01); *C12N 7/00* (2013.01); *C12N 15/86* (2013.01); *C12N 2710/24122* (2013.01); *C12N 2710/24134* (2013.01)

(58) Field of Classification Search
None
See application file for complete search history.

(56) References Cited

U.S. PATENT DOCUMENTS

| | | | | |
|---|---|---|---|---|
| 2005/0208074 A1* | 9/2005 | Balloul | ............... | C07K 14/005 424/232.1 |
| 2006/0003316 A1* | 1/2006 | Simard | ............... | A61K 39/12 435/5 |
| 2006/0062800 A1* | 3/2006 | Cohen | ............... | A61K 39/285 424/186.1 |
| 2009/0269365 A1* | 10/2009 | Koelle et al. | ............... | 424/186.1 |
| 2010/0021484 A1* | 1/2010 | Cohen | ............... | A61K 39/285 424/184.1 |
| 2010/0196491 A1* | 8/2010 | Hooper | ............... | A61K 9/0019 424/490 |
| 2011/0081368 A1* | 4/2011 | Hooper | ............... | A61K 9/0019 424/186.1 |

FOREIGN PATENT DOCUMENTS

WO    WO 2005 013918    * 2/2005

OTHER PUBLICATIONS

GenBank Accession# CAM58361, EEV type 1 membrane protein [Vaccinia virus Ankara], 2009.*
GenBank Accession# YP_232970, IMV membrane protein [Vaccinia virus], 2010.*
GenBank Accession# AAW23871, EEV glycoprotein [Vaccinia virus], 2005.*
GenBank Accession# Q9JF44, RecName: Full=Plaque-size/host range protein; AltName: Full=Protein B5; Flags: Precursor, 2010.*
GenBank Accession# AAF33948, TL1R [Vaccinia virus Tian Tan], 2000.*
Artenstein et al., "Smallpox vaccines for biodefense: need and feasibility," Expert Reviews Vaccines, vol. 7(8), Oct. 2008, pp. 1225-1237.
Bell et al., "Antibodies against the extracellular enveloped virus B5R protein are mainly responsible for the EEV neutralizing capacity of vaccinia immune globulin," Virology, vol. 325(2), Aug. 2004, pp. 425-431.
Belyakov et al., "Mucosal immunization with HIV-1 peptide vaccine induces mucosal and systemic cytotoxic T lymphocytes and protective immunity in mice against intrarectal recombinant HIV-vaccinia challenge," Proceedings of the National Academy Sciences of the U.S.A., vol. 95(4), Feb. 1998, pp. 1709-1714.
Chung et al., "A27L Protein Mediates Vaccinia Virus Interaction with Cell Surface Heparin Sulfate," Journal of Virology, vol. 72(2), Feb. 1998, pp. 1577-1585.
Crotty et al., "Cutting edge: Long-Term B Cell Memory in Humans after Smallpox Vaccination," The Journal of Immunology, vol. 171(10), Nov. 2003, pp. 4969-4973.
Davies et al., "Antibody Profiling by Proteome Microarray Reveals the Immunogenicity of the Attenuated Smallpox Vaccine Modified Vaccinia Virus Ankara is Comparable to that of Dryvax," Journal of Virology, vol. 82(2), Jan. 2008, pp. 652-663.
Davies et al., "Proteome-wide analysis of the serological response to vaccinia and smallpox," Proteomics, vol. 7(10), May 2007, pp. 1678-1686.
Di Giulio et al., "Human monkeypox: an emerging zoonosis," The Lancet Infectious Diseases, vol. 4, Jan. 2004, pp. 15-25.
Drexler et al., "Identification of vaccinia virus epitope-specific HLA-A*0201-restricted T cells and comparative analysis of smallpox vaccines," Proceedings of the National Academy Sciences of the U.S.A., vol. 100(1), Dec. 2003, pp. 217-222.
Ennis et al., "Primary Induction of Human CD8+ Cytotoxic T Lymphocytes and Interferon-γ-Producing T Cells after Smallpox Vaccination," The Journal of Infectious Diseases, vol. 185(11), May 2002, pp. 1657-1659.

(Continued)

Primary Examiner — Benjamin P Blumel
(74) Attorney, Agent, or Firm — Fish & Richardson P.C.

(57) ABSTRACT

This document provides methods and materials related to polypeptides present in a vaccinia virus (e.g., membrane proteins such as vaccinia virus B5R, L1R, A33R, or A27L polypeptides). For example, methods for generating a vaccine comprising one or more of vaccinia virus polypeptides disclosed herein for preventing or treating Orthopoxvirus infection are provided. In addition, kits related to the use of vaccinia polypeptides are provided.

5 Claims, 6 Drawing Sheets

(56) References Cited

OTHER PUBLICATIONS

Fogg et al., "Protective Immunity to Vaccinia Virus Induced by Vaccination with Multiple Recombinant Outer Membrane Proteins of Intracellular and Extracellular Virions," Journal of Virology, vol. 78(19), Oct. 2004, pp. 10230-10237.

Hammarlund et al., "Duration of antiviral immunity after smallpox vaccination," Nature Medicine, vol. 9(9), Aug. 2003, pp. 1131-1137.

Hooper et al., "Four-gene-combination DNA vaccine protects mice against a lethal vaccinia virus challenge and elicits appropriate antibody responses in nonhuman primates," Virology, vol. 306(1), Feb. 2003, pp. 181-195.

Hooper et al., "DNA Vaccination with Vaccinia Virus L1R and A33R Genes Protects Mice against a Lethal Poxvirus Challenge," Virology, vol. 266(2), Jan. 2000, pp. 329-339.

Isaacs et al., "Characterization of a Vaccinia Virus-Encoded 42-Kilodalton Class I Membrane Glycoprotein Component of the Extracellular Virus Envelope," Journal Virology, vol. 66(12), Dec. 1992, pp. 7217-7224.

Jackson et al., "A totally synthetic vaccine of generic structure that targets Toll-like receptor 2 on dendritic cells and promotes antibody or cytotoxic T cell responses," Proceedings of the National Academy Sciences of the U.S.A., vol. 101(43), Oct. 2004, pp. 15440-15445.

Kennedy et al., "Smallpox Vaccines for Biodefense," Vaccine, 27(Suppl 4), Nov. 2009, pp. D73-D79.

Kennedy et al., "Statistical Approach to Estimate Vaccinia-Specific Neutralizing Antibody Titers Using a High-Throughput Assay," Clinical and Vaccine Immunology, vol. 16(8), Aug. 2009, pp. 1105-1112.

Kennedy et al., "The identification of HLA class II-restricted T cell epitopes to vaccinia virus membrane proteins," Virology, vol. 408(2), Jun. 2010, pp. 232-240.

Manischewitz et al., "Development of a Novel Vaccinia-Neutralization Assay Based on Reporter-Gene Expression," The Journal of Infectious Diseases, vol. 188(3), Aug. 2003, pp. 440-448.

Otero et al., "Efficacy of novel plasmid DNA encoding vaccinia antigens in improving current smallpox vaccination strategy," Vaccine, vol. 24(21), May 2006, pp. 4461-4470.

Roeder et al., "Optimized determination of T cell epitope responses," Journal of Immunological Methods, vol. 274(1-2), Mar. 2003, pp. 221-228.

Roper et al., "The Envelope Protein Encoded by the A33R Gene Is Required for Formation of Actin-Containing Microvilli and Efficient Cell-to-Cell Spread of Vaccinia Virus," Journal of Virology, vol. 72(5), May 1998, pp. 4192-4204.

Ryan et al., "Detection of Measles Virus-Specific Interferon-γ-Secreting T-Cells by ELISPOT," Methods in Molecular Biology, vol. 302, 2005, pp. 207-218.

Ryan et al., "Inter-operator variation in ELISPOT analysis of measles virus-specific IFN-γ-secreting T cells," Scandinavian Journal of Clinical & Laboratory Investigation, vol. 65(8), 2005, pp. 681-689.

Sidney et al., "Quantitative peptide binding motifs for 19 human and mouse MHC class I molecules derived using positional scanning combinatorial peptide libraries," Immunome Research, 4(2), Jan. 2008, 14 pp.

Sirven et al., "In vitro human CD4+ T cell response to the vaccinia protective antigens B5R and A33R," Molecular Immunology, vol. 46(7), Apr. 2009, pp. 1481-1487.

Snyder et al., "Protection against Lethal Vaccinia Virus Challenge in HLA-A2 Transgenic Mice by Immunization with a Single CD8+ T-Cell Peptide Epitope of Vaccinia and Variola Viruses," Journal of Virology, vol. 78(13), Jul. 2004, pp. 7052-7060.

Tang et al., "Human T-cell Responses to Vaccinia Virus Envelope Proteins," Journal of Virology, vol. 80(20), Oct. 2006, pp. 10010-10020.

Wolffe et al., "A Myristylated Membrane Protein Encoded by the Vaccinia Virus L1R Open Reading Frame is the Target of Potent Neutralizing Monoclonal Antibodies," Virology, vol. 211(1), Aug. 1995, pp. 53-63.

* cited by examiner

SEQUENCE LISTING

<160> NUMBER OF SEQ ID NOS: 45

<210> SEQ ID NO 1
<211> LENGTH: 16
<212> TYPE: PRT
<213> ORGANISM: Vaccinia virus

<400> SEQUENCE: 1

Lys Ala Asp Glu Asp Asp Asn Glu Glu Thr Leu Lys Gln Arg Leu Thr
1 5 10 15

<210> SEQ ID NO 2
<211> LENGTH: 16
<212> TYPE: PRT
<213> ORGANISM: Vaccinia virus

<400> SEQUENCE: 2

Val Tyr Ser Thr Cys Thr Val Pro Thr Met Asn Asn Ala Lys Leu Thr
1 5 10 15

-continued

```
<210> SEQ ID NO 3
<211> LENGTH: 16
<212> TYPE: PRT
<213> ORGANISM: Vaccinia virus

<400> SEQUENCE: 3

Cys Thr Val Pro Thr Met Asn Asn Ala Lys Leu Thr Ser Thr Glu Thr
 1               5                  10                  15

<210> SEQ ID NO 4
<211> LENGTH: 16
<212> TYPE: PRT
<213> ORGANISM: Vaccinia virus

<400> SEQUENCE: 4

Leu Tyr Asn Lys Pro Leu Tyr Glu Val Asn Ser Thr Met Thr Leu Ser
 1               5                  10                  15

<210> SEQ ID NO 5
<211> LENGTH: 16
<212> TYPE: PRT
<213> ORGANISM: Vaccinia virus

<400> SEQUENCE: 5

Pro Asn Ala Val Cys Glu Thr Asp Lys Trp Lys Tyr Glu Asn Pro Cys
 1               5                  10                  15

<210> SEQ ID NO 6
<211> LENGTH: 16
<212> TYPE: PRT
<213> ORGANISM: Vaccinia virus

<400> SEQUENCE: 6

Cys Tyr Ile Leu His Ser Asp Tyr Gln Leu Phe Ser Asp Ala Lys Ala
 1               5                  10                  15

<210> SEQ ID NO 7
<211> LENGTH: 16
<212> TYPE: PRT
<213> ORGANISM: Vaccinia virus

<400> SEQUENCE: 7

Ala Lys Leu Thr Ser Thr Glu Thr Ser Phe Asn Asn Asn Gln Lys Val
 1               5                  10                  15

<210> SEQ ID NO 8
<211> LENGTH: 16
<212> TYPE: PRT
<213> ORGANISM: Vaccinia virus

<400> SEQUENCE: 8

Cys Glu Thr Asp Lys Trp Lys Tyr Glu Asn Pro Cys Lys Lys Met Cys
 1               5                  10                  15

<210> SEQ ID NO 9
<211> LENGTH: 16
<212> TYPE: PRT
<213> ORGANISM: Vaccinia virus

<400> SEQUENCE: 9

Thr Val Tyr Gly Asp Lys Ile Gln Gly Lys Asn Lys Arg Lys Arg Val
 1               5                  10                  15
```

-continued

```
<210> SEQ ID NO 10
<211> LENGTH: 16
<212> TYPE: PRT
<213> ORGANISM: Vaccinia virus

<400> SEQUENCE: 10

Lys Ile Thr Asn Val Thr Thr Lys Phe Glu Gln Ile Glu Lys Cys Cys
1               5                   10                  15

<210> SEQ ID NO 11
<211> LENGTH: 16
<212> TYPE: PRT
<213> ORGANISM: Vaccinia virus

<400> SEQUENCE: 11

Ala Phe Leu Ile Val Arg Leu Asn Gln Cys Met Ser Ala Asn Glu Ala
1               5                   10                  15

<210> SEQ ID NO 12
<211> LENGTH: 16
<212> TYPE: PRT
<213> ORGANISM: Vaccinia virus

<400> SEQUENCE: 12

Ser Ser Thr Thr Gln Tyr Asp His Lys Glu Ser Cys Asn Gly Leu Tyr
1               5                   10                  15

<210> SEQ ID NO 13
<211> LENGTH: 16
<212> TYPE: PRT
<213> ORGANISM: Vaccinia virus

<400> SEQUENCE: 13

Ser Gly Ser Thr Phe Ser Ile Gly Gly Val Ile His Leu Ser Cys Lys
1               5                   10                  15

<210> SEQ ID NO 14
<211> LENGTH: 16
<212> TYPE: PRT
<213> ORGANISM: Vaccinia virus

<400> SEQUENCE: 14

Cys Asn Leu Thr Val Lys Asn Met Cys Ser Ala Asp Ala Asp Ala Gln
1               5                   10                  15

<210> SEQ ID NO 15
<211> LENGTH: 16
<212> TYPE: PRT
<213> ORGANISM: Vaccinia virus

<400> SEQUENCE: 15

Asn Cys Ala Ile Lys Ala Leu Met Gln Leu Thr Thr Lys Ala Thr Thr
1               5                   10                  15

<210> SEQ ID NO 16
<211> LENGTH: 16
<212> TYPE: PRT
<213> ORGANISM: Vaccinia virus

<400> SEQUENCE: 16

Lys Cys Asp Ile Glu Ile Gly Asn Phe Tyr Ile Arg Gln Asn His Gly
1               5                   10                  15
```

-continued

```
<210> SEQ ID NO 17
<211> LENGTH: 16
<212> TYPE: PRT
<213> ORGANISM: Vaccinia virus

<400> SEQUENCE: 17

Gln Asn Val Ile Ile Asp Glu Cys Tyr Gly Ala Pro Gly Ser Pro Thr
1               5                   10                  15

<210> SEQ ID NO 18
<211> LENGTH: 16
<212> TYPE: PRT
<213> ORGANISM: Vaccinia virus

<400> SEQUENCE: 18

Gly Val Ile Phe Leu Ile Ser Val Ile Val Leu Val Cys Ser Cys Asp
1               5                   10                  15

<210> SEQ ID NO 19
<211> LENGTH: 16
<212> TYPE: PRT
<213> ORGANISM: Vaccinia virus

<400> SEQUENCE: 19

Ala Ala Leu Phe Met Tyr Tyr Ala Lys Arg Met Leu Phe Thr Ser Thr
1               5                   10                  15

<210> SEQ ID NO 20
<211> LENGTH: 16
<212> TYPE: PRT
<213> ORGANISM: Vaccinia virus

<400> SEQUENCE: 20

Ile Arg Ile Ser Met Val Ile Ser Leu Leu Ser Met Ile Thr Met Ser
1               5                   10                  15

<210> SEQ ID NO 21
<211> LENGTH: 16
<212> TYPE: PRT
<213> ORGANISM: Vaccinia virus

<400> SEQUENCE: 21

Glu Val Leu Phe Arg Leu Glu Asn His Ala Glu Thr Leu Arg Ala Ala
1               5                   10                  15

<210> SEQ ID NO 22
<211> LENGTH: 16
<212> TYPE: PRT
<213> ORGANISM: Vaccinia virus

<400> SEQUENCE: 22

Glu Gln Thr Ser Val Phe Ser Ala Thr Val Tyr Gly Asp Lys Ile Gln
1               5                   10                  15

<210> SEQ ID NO 23
<211> LENGTH: 16
<212> TYPE: PRT
<213> ORGANISM: Vaccinia virus

<400> SEQUENCE: 23

Asp Lys Ile Gln Gly Lys Asn Lys Arg Lys Arg Val Ile Gly Leu Cys
1               5                   10                  15
```

```
<210> SEQ ID NO 24
<211> LENGTH: 16
<212> TYPE: PRT
<213> ORGANISM: Vaccinia virus

<400> SEQUENCE: 24

Phe Ser Ile Gly Gly Val Ile His Leu Ser Cys Lys Ser Gly Phe Ile
1               5                   10                  15

<210> SEQ ID NO 25
<211> LENGTH: 16
<212> TYPE: PRT
<213> ORGANISM: Vaccinia virus

<400> SEQUENCE: 25

Lys Leu Glu Gln Glu Ala Asn Ala Ser Ala Gln Thr Lys Cys Asp Ile
1               5                   10                  15

<210> SEQ ID NO 26
<211> LENGTH: 16
<212> TYPE: PRT
<213> ORGANISM: Vaccinia virus

<400> SEQUENCE: 26

Ile Thr Ile Asn Cys Asp Val Gly Tyr Glu Val Ile Gly Ala Ser Tyr
1               5                   10                  15

<210> SEQ ID NO 27
<211> LENGTH: 16
<212> TYPE: PRT
<213> ORGANISM: Vaccinia virus

<400> SEQUENCE: 27

Ile Ile Val Ala Leu Thr Ile Met Gly Val Ile Phe Leu Ile Ser Val
1               5                   10                  15

<210> SEQ ID NO 28
<211> LENGTH: 16
<212> TYPE: PRT
<213> ORGANISM: Vaccinia virus

<400> SEQUENCE: 28

Lys Ala Thr Thr Gln Ile Ala Pro Arg Gln Val Ala Gly Thr Gly Val
1               5                   10                  15

<210> SEQ ID NO 29
<211> LENGTH: 16
<212> TYPE: PRT
<213> ORGANISM: Vaccinia virus

<400> SEQUENCE: 29

Met Tyr Tyr Ala Lys Arg Met Leu Phe Thr Ser Thr Asn Asp Lys Ile
1               5                   10                  15

<210> SEQ ID NO 30
<211> LENGTH: 16
<212> TYPE: PRT
<213> ORGANISM: Vaccinia virus

<400> SEQUENCE: 30

Asp Thr Phe Phe Arg Thr Ser Pro Met Val Ile Ala Thr Thr Asp Met
1               5                   10                  15
```

```
<210> SEQ ID NO 31
<211> LENGTH: 16
<212> TYPE: PRT
<213> ORGANISM: Vaccinia virus

<400> SEQUENCE: 31

Gln Ile Ala Pro Arg Gln Val Ala Gly Thr Gly Val Gln Phe Tyr Met
1               5                   10                  15

<210> SEQ ID NO 32
<211> LENGTH: 16
<212> TYPE: PRT
<213> ORGANISM: Vaccinia virus

<400> SEQUENCE: 32

Lys Arg Met Leu Phe Thr Ser Thr Asn Asp Lys Ile Lys Leu Ile Leu
1               5                   10                  15

<210> SEQ ID NO 33
<211> LENGTH: 16
<212> TYPE: PRT
<213> ORGANISM: Vaccinia virus

<400> SEQUENCE: 33

Ala Asn Lys Glu Asn Val His Trp Thr Thr Tyr Met Asp Thr Phe Phe
1               5                   10                  15

<210> SEQ ID NO 34
<211> LENGTH: 16
<212> TYPE: PRT
<213> ORGANISM: Vaccinia virus

<400> SEQUENCE: 34

Val Ile Ile Leu Ala Ala Leu Phe Met Tyr Tyr Ala Lys Arg Met Leu
1               5                   10                  15

<210> SEQ ID NO 35
<211> LENGTH: 16
<212> TYPE: PRT
<213> ORGANISM: Vaccinia virus

<400> SEQUENCE: 35

Asn Val His Trp Thr Thr Tyr Met Asp Thr Phe Phe Arg Thr Ser Pro
1               5                   10                  15

<210> SEQ ID NO 36
<211> LENGTH: 16
<212> TYPE: PRT
<213> ORGANISM: Vaccinia virus

<400> SEQUENCE: 36

Thr Thr Tyr Met Asp Thr Phe Phe Arg Thr Ser Pro Met Val Ile Ala
1               5                   10                  15

<210> SEQ ID NO 37
<211> LENGTH: 16
<212> TYPE: PRT
<213> ORGANISM: Vaccinia virus

<400> SEQUENCE: 37

Lys Ala Asp Gly Asp Asp Asn Glu Glu Thr Leu Lys Gln Arg Leu Thr
1               5                   10                  15
```

```
<210> SEQ ID NO 38
<211> LENGTH: 16
<212> TYPE: PRT
<213> ORGANISM: Vaccinia virus

<400> SEQUENCE: 38

Leu Tyr Asn Lys Pro Leu Tyr Glu Val Asn Ala Ile Ile Thr Leu Ile
 1               5                   10                  15

<210> SEQ ID NO 39
<211> LENGTH: 16
<212> TYPE: PRT
<213> ORGANISM: Vaccinia virus

<400> SEQUENCE: 39

Cys Tyr Ile Phe His Ser Asp Tyr Gln Leu Phe Ser Asp Ala Lys Ala
 1               5                   10                  15

<210> SEQ ID NO 40
<211> LENGTH: 16
<212> TYPE: PRT
<213> ORGANISM: Vaccinia virus

<400> SEQUENCE: 40

Ala Lys Leu Thr Ser Thr Glu Thr Ser Phe Asn Asp Lys Gln Lys Val
 1               5                   10                  15

<210> SEQ ID NO 41
<211> LENGTH: 16
<212> TYPE: PRT
<213> ORGANISM: Vaccinia virus

<400> SEQUENCE: 41

Ser Ser Thr Thr Gln Tyr Lys His Gln Glu Ser Cys Asn Gly Leu Tyr
 1               5                   10                  15

<210> SEQ ID NO 42
<211> LENGTH: 16
<212> TYPE: PRT
<213> ORGANISM: Vaccinia virus

<400> SEQUENCE: 42

Gly Val Ile Phe Leu Ile Ser Val Ile Val Leu Val Cys Ser Cys Asn
 1               5                   10                  15

<210> SEQ ID NO 43
<211> LENGTH: 16
<212> TYPE: PRT
<213> ORGANISM: Vaccinia virus

<400> SEQUENCE: 43

Asp Val Leu Phe Arg Leu Glu Asn His Ala Glu Thr Leu Arg Ala Ala
 1               5                   10                  15

<210> SEQ ID NO 44
<211> LENGTH: 16
<212> TYPE: PRT
<213> ORGANISM: Vaccinia virus

<400> SEQUENCE: 44

Asp Lys Ile Gln Gly Lys Asn Lys Arg Lys Arg Val Ile Gly Ile Cys
 1               5                   10                  15
```

```
<210> SEQ ID NO 45
<211> LENGTH: 16
<212> TYPE: PRT
<213> ORGANISM: Vaccinia virus

<400> SEQUENCE: 45

Asp Thr Phe Phe Arg Thr Ser Pro Met Val Ile Ala Thr Thr Asp Ile
1               5                   10                  15
```

US 9,446,119 B2

VACCINIA VIRUS POLYPEPTIDES

CROSS REFERENCED TO RELATED APPLICATIONS

This application claims the benefit of U.S. Provisional Application Ser. No. 61/529,739, filed Aug. 31, 2011. The disclosure of the prior application is considered part of (and is incorporated by reference in) the disclosure of this application.

STATEMENT AS TO FEDERALLY SPONSORED RESEARCH

This invention was made with government support under AI057153 awarded by the National Institutes of Health. The government has certain rights in the invention.

BACKGROUND

1. Technical Field

This document provides methods and materials relating to isolated vaccinia virus-derived polypeptides. For example, this document relates to specific and naturally processed and HLA presented vaccinia virus-derived polypeptides isolated from a membrane polypeptide such as B5R, L1R, A33R, and A27L of vaccinia virus, a member of the Orthopoxvirus family. This document provides methods and materials for generating a vaccine for preventing or treating an Orthopoxvirus infection that induces a protective therapeutic immune response. The vaccines can include one or more of the isolated vaccinia virus polypeptides provided herein. In some cases, this document provides kits related to the use of vaccinia virus polypeptides.

2. Background Information

Polypeptide-based vaccines use small polypeptide sequences derived from target proteins as epitopes to provoke an immune reaction. These vaccines are a result of an improved understanding of the molecular basis of epitope recognition, thereby permitting the development of rationally designed, epitope-specific vaccines based on motifs demonstrated to bind to human class I (HLA I) or class II (HLA II) major histocompatibility complex (MHC) molecules. Of particular interest has been the discovery of epitopes that are specifically recognized by T cells for prophylaxis and treatment of infectious diseases.

Over the centuries, naturally occurring smallpox, with its case-fatality rate of 30 percent or more and its ability to spread in any climate and season, has been universally feared as one of the most devastating of all the infectious diseases. The use of vaccinia virus as a vaccine enabled the global eradication of naturally occurring smallpox. The last naturally occurring case of smallpox occurred in Somalia in 1977. In May 1980, the World Health Assembly certified that the world was free of naturally occurring smallpox. Routine vaccination against smallpox in the United States ended in 1971, and except for some soldiers and laboratory workers, no one has been vaccinated since 1983. However, terrorist activities in the early 21st century as well as imported outbreaks of monkeypox (a member of the Orthopox virus family) in the USA, spurred renewed interest in biodefense countermeasures for these public health threats (Artenstein et al., *Expert Rev. Vaccines*, 7:1225-1237 (2008) and Giulio et al., *Lancet Infect. Dis.*, 4:15-25 (2004)).

SUMMARY

This document provides methods and materials related to vaccinia virus polypeptides. For example, this document provides vaccinia virus polypeptides that have the ability to be naturally processed and presented by HLA molecules. For example, this document provides compositions containing one or more polypeptides that have a sequence that is present in a vaccinia virus membrane polypeptide such as a vaccinia virus B5R, L1R, A33R, or A27L polypeptide. This document also provides methods and materials (e.g., vaccines) for preventing or treating Orthopoxvirus infections. For example, the vaccines provided herein can include one or more of the vaccinia virus polypeptides provided herein and can have the ability to induce a protective therapeutic immune response within a mammal (e.g., a human). In addition, this document provides kits related to the use of vaccinia virus polypeptides.

As described herein, 36 viral epitopes were identified in vaccinia virus membrane polypeptides (e.g., B5R, L1R, A33R, and A27L). The identification of these naturally processed and presented polypeptides can be used to aid in understanding the immune process and can be used to generate vaccines against Orthopoxviruses.

In general, one aspect of this document features an isolated polypeptide, wherein the amino acid sequence of the polypeptide is as set forth in any one of SEQ ID NOs:1-36.

In another aspect, this document features a composition comprising, or consisting essentially of, at least one isolated polypeptide selected from the group consisting of SEQ ID NOs:1-18 and 19, and at least one HLA class-I restricted vaccinia virus derived polypeptide. The composition can further comprise an adjuvant.

In another aspect, this document features a method of preventing or treating a variola virus infection in a subject. The method comprises, or consists essentially of, administering to the subject a composition comprising an adjuvant and at least one polypeptide, wherein the amino acid sequence of the polypeptide is as set forth in any one of SEQ ID NOs:1-19. The subject can be a human. The method can comprise administering at least one HLA class-I restricted vaccinia virus derived polypeptide. The method can comprise administering at least one additional polypeptide, wherein the sequence of the additional polypeptide is as set forth in any one of SEQ ID NOs:20-36.

In another aspect, this document features a vaccine comprising, or consisting essentially of, at least one isolated polypeptide, wherein the amino acid sequence of the polypeptide is as set forth in any one of SEQ ID NOs:1-19. The vaccine can comprise at least one HLA class-I restricted vaccinia virus derived polypeptide. The vaccine can comprise an adjuvant.

In another aspect, this document features a method of inducing an immune response against at least one isolated polypeptide, wherein the sequence of the polypeptide is as set forth in any one of SEQ ID NOs:1-19. The method comprises, or consists essentially of, administering the polypeptide to a subject in an amount effective to induce an immune response against the polypeptide. The polypeptide can be administered in combination with at least one HLA class-I restricted vaccinia virus derived polypeptide. The polypeptide can be administered in combination with at least one additional polypeptide, wherein the sequence of the additional polypeptide is as set forth in any one of SEQ ID NOs:20-36. The polypeptide can be administered in combination with a pharmaceutically acceptable excipient, carrier, diluent, or vehicle. The immune response can be a cell mediated immune response.

In another aspect, this document features a kit comprising, or consisting essentially of, at least one polypeptide selected from the group consisting of SEQ ID NOs:1-18 and 19, and an adjuvant. The kit can comprise at least two polypeptides selected from the group. The kit can comprise at least one HLA class-I restricted vaccinia virus derived polypeptide. The kit can comprise at least one additional polypeptide, wherein the sequence of the additional polypeptide is as set forth in any one of SEQ ID NOs:20-36.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
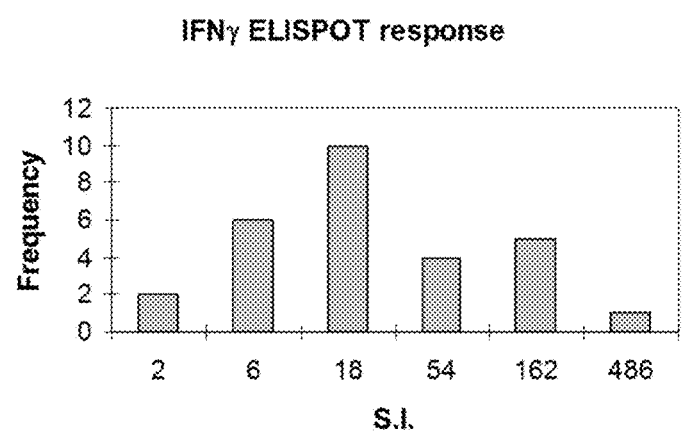
FIG. 1A is a histogram plotting the frequencies of particular ranges of IFNγ ELISPOT results as stimulation index (S.I.). S.I. refers to the average spot forming units in vaccinia stimulated wells divided by the average spot forming units in background wells. The X-axis scale indicates the upper bound of each bin (i.e., two subjects had an S.I. less than 2, and six subjects had S.I. values between 2.1 and 6).

This document provides methods and materials related to vaccinia virus polypeptides. For example, this document provides vaccinia virus polypeptides that have the ability to be naturally processed and presented by HLA molecules. In some cases, a polypeptide provided herein can have a sequence present in a vaccinia virus membrane polypeptide such as a B5R, L1R, A33R, or A27L polypeptide. This document also provides methods and materials (e.g., vaccines) for preventing or treating Orthopoxvirus infections. For example, the vaccines provided herein can include one or more of the vaccinia virus polypeptides provided herein and can have the ability to induce a protective therapeutic immune response within a mammal (e.g., a human). In addition, this document provides kits related to the use of vaccinia virus polypeptides.

A33R is a membrane glycoprotein found on the surface of enveloped virion (EV) particles. A27L is an MV membrane protein involved in cell attachment and fusion. B5R is an EV membrane protein required for the formation of EV particles. L1R is a myristylated product of a vaccinia late gene and is essential for the formation of infectious MV (Chung et al., *J. Virol.*, 72(2):1577-1585 (1998); Isaacs et al., *J. Virol.*, 66(12):7217-7224 (1992); Roper et al., *J. Virol.*, 72(5):4192-4204 (1998); and Wolffe et al., *Virology*, 211(1):53-63 (1995)). Each of these polypeptides can be targets of neutralizing antibody responses. For example, B5R can serve as a major target of EV neutralizing activity in serum samples from vaccine recipients (Bell et al., *Virology*, 325 (2):425-431 (2004)).

This document provides compositions (e.g., vaccine compositions) containing one or more vaccinia virus polypeptides provided herein. In some cases, a vaccinia virus polypeptide provided herein can have the ability to be naturally processed and presented by an MHC molecule. Examples of vaccinia virus polypeptide provided herein include, without limitation, those vaccinia virus polypeptides set forth in SEQ ID NOs:1-19 of Table 1. In some cases, the polypeptides set forth in SEQ ID NOs:1-19 can be used individually or as a mixture for the prevention and/or therapeutic treatment of Orthopoxvirus infections in vitro and in vivo, and/or for improved diagnostic detection of Orthopoxvirus infections. Any appropriate combination of the polypeptides listed in Table 1 can be used. For example, the combination can include at least 2, 3, 4, 5, 6, 7, 8, 9, 10, 11, 12, 13, 14, 15, 16, 17, 18, or more polypeptides selected from Table 1. For example, the polypeptides corresponding to SEQ ID NOs:1-10 can be used in any combination. In some cases, the polypeptides corresponding to SEQ ID NOs:1-10 and SEQ ID NOs:15-19 can be used in any combination. For example, a polypeptide having the amino acid sequence set forth in SEQ ID NO:1 and a polypeptide having the amino acid sequence set forth in SEQ ID NO:3 can be used together in any combination with one or more polypeptides of SEQ ID NOs:15-19.

In some cases, a combination of the polypeptides listed in Table 1 can be used with the exception of 2, 3, 5, 10, 15, or more polypeptides selected from Table 1. For example, the polypeptides corresponding to SEQ ID NOs:1-10 can be used in any combination with the exception of SEQ ID NOs:11-19. For example, the polypeptides corresponding to SEQ ID NOs:1-19 can be used in any combination with the exception of SEQ ID NO:1, SEQ ID NO:5, and SEQ ID NO:10.

Additional examples of vaccinia virus polypeptides provided herein include, without limitation, those vaccinia virus polypeptides set forth in SEQ ID NOs:20-36 of Table 2. In some cases, the polypeptides set forth in SEQ ID NOs:20-36 can be used individually or as a mixture for the prevention and/or therapeutic treatment of Orthopoxvirus infections in vitro and in vivo, and/or for improved diagnostic detection of Orthopoxvirus infections. Any appropriate combination of the polypeptides listed in Table 2 can be used. For example, the combination can include at least 2, 3, 4, 5, 6, 7, 8, 9, 10, 11, 12, 13, 14, 15, or more polypeptides selected from Table 2. For example, the polypeptides corresponding to SEQ ID NOs:20-30 can be used in any combination. In some cases, the polypeptides corresponding to SEQ ID NOs:20-30 and SEQ ID NOs:36-36 can be used in any combination. For example, a polypeptide having the amino acid sequence set forth in SEQ ID NO:20 and a polypeptide having the amino acid sequence set forth in SEQ ID NO:25 can be used together in any combination with one or more polypeptides of SEQ ID NOs:30-36.

In some cases, a combination of the polypeptides listed in Table 2 can be used with the exception of 2, 3, 5, 10, 15, or more polypeptides selected from Table 2. For example, the polypeptides corresponding to SEQ ID NOs:20-36 can be used in any combination with the exception of SEQ ID NOs:29-36. For example, the polypeptides corresponding to SEQ ID NOs:20-36 can be used in any combination with the exception of SEQ ID NO:20, SEQ ID NO:25, and SEQ ID NO:30.

In some cases, one or more of the polypeptides set forth in SEQ ID NOs:1-19 can be used in combination with at least one of the polypeptides set forth in SEQ ID NOs:20-36. Any appropriate combination of the polypeptides listed in Table 1 can be used with at least one of the polypeptides set forth in SEQ ID NOs:20-36. In some cases, a combination can include at least 2, 3, 5, 10, 15, or more polypeptides selected from Table 1 with at least one of the polypeptides set forth in Table 2. For example, the polypeptides corresponding to SEQ ID NOs:1-10 can be used in combination with SEQ ID NO:21. In some cases, the polypeptides corresponding to SEQ ID NOs:1-10 can be used in combination with SEQ ID NO:25. In some cases, the combination can include at least 2, 3, 5, 10, 15, or more polypeptides selected from Table 1 with at least 2, 3, 5, 10, or more polypeptides selected from Table 2. For example, the polypeptides corresponding to SEQ ID NOs:1-5 can be used in combination with SEQ ID NOs:25-30. In some cases, SEQ ID NOs:1, 5, and 10 can be used in combination with SEQ ID NOs:20, 30, and 35.

The polypeptides provided herein (e.g., the polypeptide presented in Tables 1 and 2) can include oxidized amino acid residues (e.g., oxidized forms of methionine) or can lack oxidized amino acid residues.

The term "isolated" refers to material which is substantially or essentially free from components which normally accompany the material as it is found in its native state. Thus, isolated polypeptides as described in this document do not contain materials normally associated with the polypeptides in their in situ environment. The term "polypeptide" generally refers to a short chain of amino acids linked by polypeptide bonds. Typically, polypeptides comprise amino acid chains of about 2-100, more typically about 4-50, and most commonly about 6-20 amino acids.

Any appropriate method can be used to obtain a vaccinia virus polypeptide provided herein. For example, polypeptides having the sequence set forth in any one of SEQ ID NOs:1-36 can be synthesized by methods known to one skilled in the art of making polypeptides. Of course, other methods in the art would be appropriate. In some cases, simple chemical polypeptide synthesis techniques can be used to obtain a vaccinia virus polypeptide provided herein. In some cases, a polynucleotide sequence encoding a vaccinia virus polypeptide of interest can be inserted into a plasmid or other vector that can then be delivered to hosts that can be induced to transcribe and translate the polynucleotide into the polypeptide of interest. In some cases, a polynucleotide sequence for a larger polypeptide can be inserted into host cells that can produce the larger polypeptide and then process that polypeptide into a smaller polypeptide or a functionally equivalent variant of interest.

A composition provided herein containing one or more polypeptides set forth in SEQ ID NOs:1-36 or any appropriate combination of polypeptides as described herein can be formulated to provide a polypeptide-based vaccine. In some cases, such a vaccine can be designed to be based on a combination of naturally processed and presented vaccinia virus polypeptides. For example, a polypeptide-based vaccine can be designed to include at least one polypeptide selected from SEQ ID NOs:1-19 and at least one polypeptide selected from SEQ ID NOs:20-36. Any appropriate method can be used to formulate a polypeptide-based vaccine including, for example, those methods used to formulate polypeptide-based vaccines directed against other viral targets. Examples of polypeptide-based vaccines directed to other viral targets are described elsewhere (see, e.g., Belyakov et al., *Proc. Natl. Acad. Sci. U.S.A.,* 95(4):1709-1714 (1998) and Jackson et al., *Proc. Natl. Acad. Sci. U.S.A.,* 101(43):15440-15445 (2004)). In some cases, a vaccine composition provided herein can include one or more polypeptides set forth in SEQ ID NOs:1-36 (or any appropriate combination of polypeptides as described herein) in combination with the active ingredients or polypeptides of a vaccine composition described elsewhere (see, e.g., Belyakov et al., *Proc. Natl. Acad. Sci. U.S.A.,* 95(4):1709-1714 (1998) and Jackson et al., *Proc. Natl. Acad. Sci. U.S.A.,* 101(43):15440-15445 (2004)). Such vaccine compositions can provide a level of protection against Orthopoxvirus infections as well as a level of protection against infections by other viral targets.

In some cases, a vaccine composition provided herein can be designed to prevent or treat an Orthopoxvirus infection. For example, a vaccine composition provided herein can have the ability to induce a protective or therapeutic immune response within a mammal (e.g., a human). In some cases, a vaccinia virus polypeptide provided herein can be used to provide protection against multiple members of the Orthopoxvirus family. In some cases, a vaccine composition provided herein can be directed against any Orthopoxvirus.

For example, a vaccine composition provided herein can be directed against monkeypox, cowpox, and camelpox. In some cases, a vaccine composition provided herein can be directed against vaccinia or variola major or minor. The term "vaccine" as used herein refers to immunogenic compositions that are administered to a subject for the prevention, amelioration, or treatment of diseases (e.g., infectious diseases). In some cases, one or more features of other vaccine preparations can be incorporated into a vaccine composition provided herein. For example, a polypeptide used to create a vaccinia vaccine can be included within a vaccine composition provided herein. Examples of vaccinia-specific single polypeptide vaccines that have one or more features that can be included in the methods and materials (e.g., a vaccine composition) provided herein are described elsewhere (see, e.g., Snyder et al., *J. Virol.*, 78(13):7052-60 (2004) and Drexler et al., *Proc. Natl. Acad. Sci. U.S.A.*, 100(1):217-22 (2003)).

A polypeptide provided herein (e.g., a polypeptide set forth in Table 1 or Table 2) can be formulated into a vaccine composition using any appropriate method. In some cases, a polypeptide provided herein can be combined with a pharmaceutically acceptable carrier or pharmaceutical excipient. The term "pharmaceutically acceptable" refers to a generally non-toxic, inert, and/or physiologically compatible composition. A term "pharmaceutical excipient" includes materials such as adjuvants, carriers, pH-adjusting and buffering agents, tonicity adjusting agents, wetting agents, preservatives, and the like. Examples of adjuvants include, without limitation, CpG, aluminum sulfate, aluminumphosphylate, and MF59. In some cases, vaccines or components of a vaccine can be conjugated to, for example, a polysaccharide or other molecule, to improve stability or immunogenicity of one or more vaccine components. In some cases, a polypeptide provided herein (e.g., a polypeptide set forth in Table 1 or Table 2) can be formulated into a vaccine composition containing cells. For example, one or more polypeptides provided herein can be included within a cellular vaccine. Any appropriate method can be used to prepare a cellular vaccine or the components of a cellular vaccine.

This document also provides methods and materials for treating mammals (e.g., humans) having an Orthopoxvirus infection. For example, a composition provided herein can be administered to a mammal having an Orthopoxvirus infection under condition effective to reduce the severity of one or more symptoms of the Orthopoxvirus infection. Treatment of individuals having an Orthopoxvirus infection (e.g., a vaccinia virus infection) can include the administration of a therapeutically effective amount of one or more polypeptides set forth in SEQ ID NOs:1-36. In some cases, treatment can include the use of one or more polypeptides set forth in SEQ ID NOs:1-36 individually or as a mixture. In some cases, one or more polypeptides set forth in SEQ ID NOs:1-19 can be used in combination with at least one of the polypeptides set forth in SEQ ID NOs:20-36. The polypeptides can be used or administered as a mixture, for example, in equal amounts, or individually, provided in sequence, or administered all at once. The term "therapeutically effective amount" refers to that amount of the agent sufficient to result in amelioration of symptoms, e.g., treatment, healing, prevention, or amelioration of such conditions. In providing a subject with a polypeptide provided herein (e.g., a vaccinia-derived polypeptide), combinations or fragments thereof, capable of inducing a therapeutic effect, the amount of administered agent will vary depending upon such factors as the subject's age, weight, height, sex, general medical condition, previous medical history, etc. The subject can be, for example, a mammal. The mammal can be any type of mammal including, without limitation, a mouse, rat, dog, cat, horse, sheep, goat, cow, pig, monkey, or human.

In some cases, one or more vaccinia virus polypeptides provided herein can be used to make a multivalent vaccine. For example, a multivalent vaccine can be designed to include at least one of the polypeptides described herein (or a combination of the polypeptides described herein) in combination with one or more HLA class I restricted vaccinia virus polypeptides to create a multivalent vaccine capable of stimulating helper and cytotoxic immune cells. Any combination of polypeptides can be used. In some cases, the combination can include at least 2, 3, 5, 10, 15, or more polypeptides described herein with at least 2, 3, 5, 10, 15, or more HLA class I restricted vaccinia virus polypeptides. For example, an HLA class I restricted polypeptide can be obtained from early proteins, intermediate proteins, late proteins, or combinations thereof. For example, an HLA class I restricted polypeptide can be obtained from A10L, A12L, A1L, A6L, A23R, A24R A29L, A31R, A35R, A44L, A46R, A48R, A49R, A52R, A7L, A17L, A8R, B12R, B13R, B15R, B1R, B21R, B22R, C2L, C15L, C16L, C11R, C12L, C2L, D13L, D6R, D8L, D12L, E2L, E10R, E5R, E6R, E8R, E9L, F1L, F2L, F11L, F12L, F16L, F1L, G4L, G5.5E, G5R, H4L, H5R, H7R, I1L, J3R, J4R, J6R, K1L, K3L, K6L, K7R, M1L, N1L, N2L, or O1L. In some cases, an HLA class I restricted polypeptide can be obtained from a B5R, L1R, A33R, or A27L polypeptide. For example, an HLA class I restricted polypeptide that can be used as described herein can be contained within a polypeptide sequence selected from SEQ ID NOs:1-36.

This document also provides kits that can be used for a variety of applications including, without limitation, combining reagents necessary for producing vaccine compositions. Such vaccine compositions can include one or more polypeptides provided herein (e.g., one or more vaccinia-derived polypeptide described herein) as well as adjuvants, diluents, and pharmaceutically acceptable carriers. In some cases, a kit provided herein can include a combination of vaccinia virus polypeptides (e.g., vaccinia-derived polypeptides) as described herein. In some cases, a kit provided herein can include at least 2, 3, 5, 10, 15, 20, 25, 30, or more polypeptides described herein. Any appropriate combination of the polypeptides can be used. In some cases, a kit provided herein can include one or more adjuvants and can include instructions for preparing and administering a vaccine composition.

In some cases, a kit provided herein can be designed as a diagnostic kit. For example, a kit provided herein can be designed to include reagents that can be used to detect cellular immune responses. In some cases, a kit provided herein can be designed to include polypeptides that can be used to detect antigen specific T cells. Such polypeptides (e.g., a polypeptide listed in Table 1 or 2) can be used to detect antigen specific T cells in samples from Orthopoxvirus (e.g., vaccinia virus) infected or exposed subjects. In some cases, such polypeptides (e.g., a polypeptide listed in Table 1 or 2) can be used to detect antigen specific T cells post-vaccination of a subject to determine the efficacy of immunization. For example, the polypeptides provided herein can be used to determine whether a subject's peripheral blood lymphocytes (PBLs) are capable of producing a suitable antigen-specific response. For example, the polypeptides provided herein can be used to detect HLA class-II restricted T helper cells. In some cases, polypeptide induced secretion of cytokines can be used to detect HLA class II restricted helper T cells. Examples of cytokines that can be used include, without limitation, interferon gamma (IFN-gamma), tumor necrosis factor alpha (TNF-alpha), interleukin 2 (IL-2), interleukin 4 (IL-4), interleukin 5 (IL-5), and interleukin 10 (IL-10). In some cases, polypeptide-induced degranulation can be used to detect generation of HLA class II restricted helper T cells in response to Orthopoxvirus (e.g., vaccinia virus) infection. Examples of markers that can be used to measure degranulation include, without limitation, intracellular expression of perforin, granzyme B, or cell surface expression of CD107a.

Any appropriate method can be used to detect antigen specific T cells using a polypeptide provided herein. For example, flow cytometry, enzyme-linked immunospot (ELISPOT), cytokine secretion, direct cytotoxicity assays, and lymphoproliferation assays can be used to detect antigen specific T cells using a polypeptide provided herein. In some cases, a polypeptide provided herein can be used in an MHC-peptide tetramer analysis in which isolated, fluorochrome labeled MHC-peptide tetramers are used to bind to antigen-specific T cells in PBLs, and bound cells can be counted by flow cytometry. Such kits can include at least one polypeptide provided herein. In some cases, such a kit can include at least 2, 3, 5, 10, 15, 20, 25, 30, or more polypeptides provided herein for the detection of antigen specific T cells.

The invention will be further described in the following examples, which do not limit the scope of the invention described in the claims.

EXAMPLES

Example 1

Identification of HLA Class II-Restricted T Cell Epitopes to Vaccinia Virus Membrane Proteins Materials and Methods
Subject Recruitment Healthy volunteers from Mayo Clinic who had participated in past smallpox vaccine trials or were part of the Department of Health and Human Services first responder's initiative were recruited for this study. All individuals provided informed consent and submitted to a single blood draw of 100 mL. Serum and peripheral blood mononuclear cells (PBMCs) were isolated, aliquoted, and frozen until use. Approval for the study was received from Mayo Clinic's Institutional Review Board.
Viruses and Cell Lines Vaccinia viruses (both NYCBOH and WR strain) were grown in Hela S3 cells, titrated in Vero cells and stored at −70° C. until use. Virus was inactivated using Psoralen and UV light as described elsewhere (Crotty et al., *J. Immunol.*, 171(10):4969-4973 (2003)) or heated to 52° C. for 1 hour. DC2.4 and LB27.4 cells and allogeneic splenocytes were used as MHC II positive APCs where indicated.
Peptides and Reagents A series of 16mer peptides, offset by four amino acids that spanned the length of each of the four selected viral proteins were designed. Peptides for the overlapping library were purchased from Mimotopes (Clayton, Australia), and purified peptides were synthesized at Mayo Clinic or Mimotopes. All peptides were dissolved in DMSO at 20 mg/mL and stored at −20° C. until use. Peptide pools contained equal amounts of 9-11 peptides each.

ELISPOT Assays

PBMCs were purified from whole blood using CPT tubes (Becton Dickinson Franklin Lake, N.J.). After purification, PBMCs were aliquoted and frozen in liquid nitrogen until use. Culture media consisted of RPMI (Invitrogen, Carlsbad, Calif.) supplemented with 10% FCS, penicillin/streptomycin, non-essential amino acids, sodium pyruvate and sodium bicarbonate, and 50 µM beta-mercaptoethanol. Where indicated, CD8$^+$ T cells were removed using magnetic bead separation (Miltenyi Biotec Auburn, Calif.). IFNγ ELISPOT kits were obtained from BD Biosciences (San Diego, Calif.) and assays were conducted according to established protocols (Ryan et al., *Scand. J. Clin. Lab. Invest.*, 65(8):681-689 (2005) and Ryan et al., *Methods Mol. Biol.*, 302:207-218 (2005)) adapted for monitoring vaccinia-specific responses (Ennis et al., *J. Infect. Dis.*, 185(11):1657-1659 (2002) and Hammarlund et al., *Nat. Med.*, 9(9):1131-1137 (2003)). Briefly, 200,000 PBMCs were plated in each well. Peptide pools (consisting of 9-11 peptides each) were added at a final concentration of ~10 µg/mL, while individual peptides were added at concentration of 30 µg/mL. Vaccinia virus was inactivated with Psoralen and UV light (Crotty et al, *J. Immunol.*, 171(10):4969-4973 (2003)) and inactivated viral particles were added to individual wells at an MOI of 5.0 (based on pre-inactivation titration). Plates were incubated for 24 hours, washed, and developed as per manufacturer's instructions. All plates were then scanned and analyzed on an ImmunoSpot® S4 Pro Analyzer (Cellular Technology Ltd., Cleveland, Ohio, USA) using ImmunoSpot® version 4.0 software (Cellular Technology Ltd.).
Statistical Analyses For ELISPOT assays, the number of spots per million cells was calculated for each well. The average spot number per experimental group was compared to the negative control wells (medium alone or DMSO) using a two-tailed student's t test. Positive responses were defined as those with an average spot number 1.5 fold over background values and with p≤0.05. The peptides reported herein had positive results in at least two separate experiments. For the initial screening of peptide pools, a more generous p-value of 0.10 was used. False positive results were minimized by the more rigorous statistical standards in the subsequent screening of individual peptides and the requirement for positive signals in multiple experiments.
Results
Protein Selection and Library Screening A list of viral proteins known to be targeted by humoral responses to vaccinia was compiled (Davies et al., *Proteomics*, 7(10):1678-1686 (2007) and Davies et al., *J. Virol.*, 82(2):652-663 (2008)). From this list of over a dozen proteins, four were selected (A33R, A27L, B5R, and L1R) for further study. See, e.g., Fogg et al., *J. Virol.*, 78(19): 10230-10237 (2004); Hopper et al., *Virology*, 266(2):329-339 (2000); Hooper et al., *Virology*, 306(1):181-195 (2003); and Tang et al., *J. Virol.*, 80(20): 10010-10020 (2006)). Overlapping peptide libraries spanning the amino acid sequence for each protein were synthesized and divided into pools using the Deconvolute This software (courtesy of Mario Roederer, NIH) (Roeder and Koup, *J. Immunol. Methods*, 274(1-2):221-228 (2003)). Each peptide was placed into three separate pools to allow for more rapid deconvolution of positive responses. Twenty-nine individuals who had received the smallpox vaccine within the last four years were recruited.
Immune Responses to Vaccinia Virus Humoral immunity was measured using a reporter-based neutralizing antibody assay (Kennedy et al., *Clin. Vaccine*

Figure 1B:
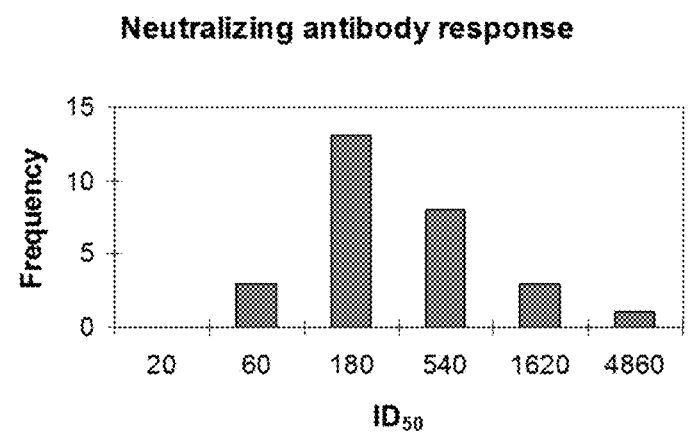
FIG. 1B is a histogram plotting the frequencies of 50% inhibitory dose ($ID_{50}$) results. $ID_{50}$ refers to the reciprocal of the serum dilution that inhibits 50% of viral activity. X-axis scale indicates upper bound of each bin (i.e., no subjects had $ID_{50}$ values less than 20, while three subjects had an $ID_{50}$ between 21 and 60).

*Immunol.*, 16(8):1105-1112 (2009) and Manischewitz et al., *J. Infect. Dis.*, 188(3):440-448 (2003)). All of the subjects had detectable levels of vaccinia neutralizing antibody, with $ID_{50}$ (the serum dilution which neutralizes 50% of viral activity) values ranging from 37.3 to 1631.6 (FIG. 1). Each of these values was significantly greater than those seen in vaccinia-naïve individuals ($ID_{50}$ values routinely below 5.0) (Kennedy et al., *Vaccine*, 27(Suppl 4):D73-D79 (2009)). All but two of the 29 subjects enrolled in this study exhibited vaccinia-specific T cell responses (S.I.>2) as measured by IFN-γ ELISPOT assay. Spots per million cells in vaccinia stimulated wells were divided by the spots per million cells in background wells to provide the stimulation index (S.I.) which ranged from 1.22 to 444.0 (FIG. 1), reflecting a large spectrum of cellular immune responses.

Immune Responses to Viral Peptides and Epitope Identification

Figure 2:
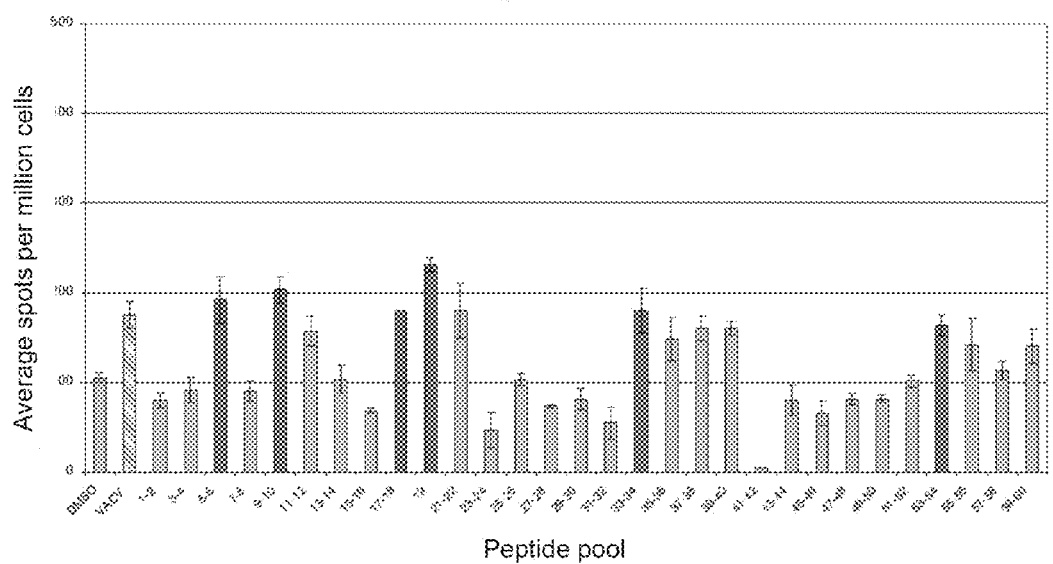
FIG. 2 is a graph plotting the immune responses (average spots per million cells) of a single individual to the indicated pooled peptides. Similar results were seen for all individuals tested. Bars indicate the average number of IFNγ producing spots for wells (3-5 replicates) stimulated with the antigen (total peptide concentration: 10 μg/mL) indicated on the X-axis. Error bars represent the standard deviation. Dark gray bars indicate responses significantly above background ($p \leq 0.05$).
Figure 3:
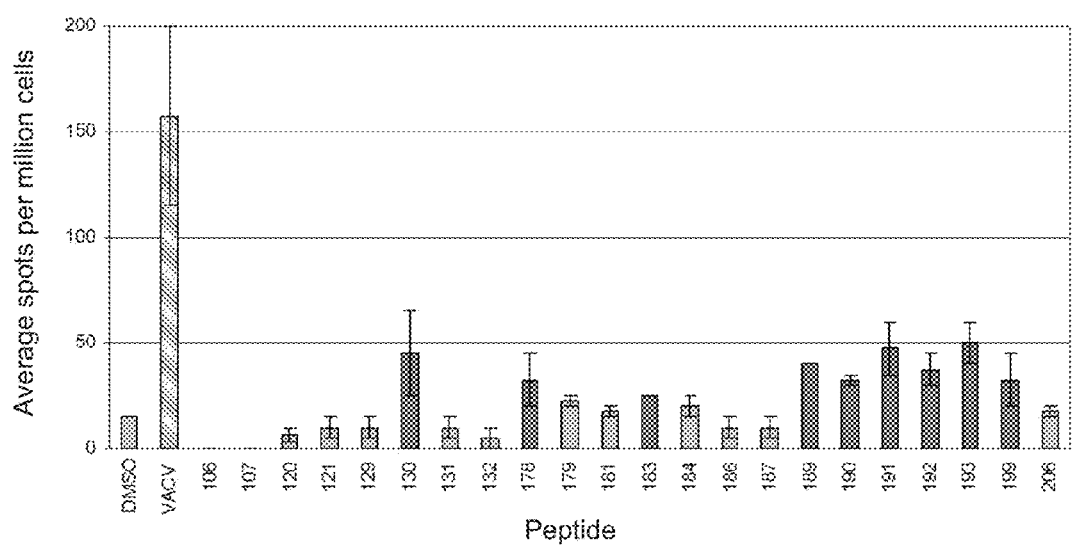
FIG. 3 is a graph plotting the immune responses (average spots per million cells) of the individual shown in FIG. 2 to the indicated individual peptides. The positive pools shown in FIG. 2 were used to select peptides for individual screening. Graph layout is as described in FIG. 2.
Figure 4:
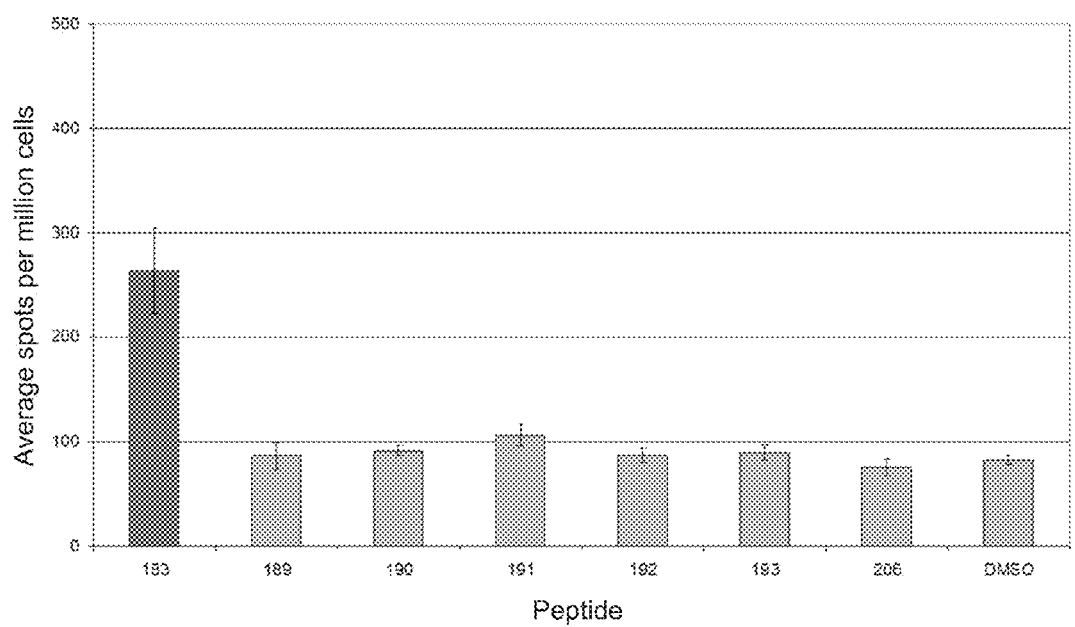
FIG. 4 is a graph plotting CD4$^+$ T cell responses (average spots per million cells) of the individual shown in FIG. 2 to selected peptides. Prior to stimulation with the indicated peptides (X-axis), CD8$^+$ T cells were removed by magnetic bead depletion. The resulting cell populations contained <2 percent CD8$^+$ T cells. The graph layout is as described in FIG. 2.

Immune responses to peptide pools were tested in IFN-γ ELISPOT assays using cells from these individuals. A representative example of the immune response profile is shown in FIG. 2. Positive pools were identified, and the individual peptides potentially contributing to the response profile were identified using the Deconvolute This software. These potential epitopes were then screened individually or in smaller pools depending on the number of possible candidates (FIG. 3). Positive peptides were confirmed in follow-up experiments using cells depleted of $CD8^+$ T lymphocytes (FIG. 4). One of the benefits of using overlapping peptide libraries for epitope mapping was that it allowed one to test all possible HLA class I and class II peptides without regard for allele-specific binding restrictions.

Nearly all (28/29) subjects demonstrated significant T cell responses to peptide pools, indicative of cellular immune responses to these four proteins. Individual epitope-specific responses in nearly one-half of the responders (13/28) were identified. The remaining subjects had significant immune responses to pooled peptides but not to individual peptides, indicating that these initial responses were either false positives or that they represented the combined, synergistic effect of multiple epitope-specific T cell populations which, when analyzed individually, fell below the level of detection of the assays. The epitope mapping results are shown in Table 1 and Table 2.

TABLE 1

Characteristics of identified MHC II-restricted T helper epitopes.

| SEQ ID NO: | Poly-peptide #[a] | Sequence[b] | Protein[c] | VARV sequence[d] | Protein sequence homology[e] | | | |
|---|---|---|---|---|---|---|---|---|
| | | | | | VACV | VARV | MPXV | CMLV |
| 1 | 1 | KADEDDNEETLKQRLT | A27L | KADGDDNEETLKQRLT (SEQ ID NO: 37) | 99.5 | 98.1 | 94.6 | 97.3 |
| 2 | 2 | VYSTCTVPTMNNAKLT | B5R | VYSTCTVPTMNNAKLT | 98.6 | 93.6 | 96.8 | 93.1 |
| 3 | 3 | CTVPTMNNAKLTSTET | B5R | CTVPTMNNAKLTSTET | 98.6 | 93.6 | 96.8 | 93.1 |
| 4 | 4 | LYNKPLYEVNSTMTLS | B5R | LYNKPLYEVNAIITLI (SEQ ID NO: 38) | 98.6 | 93.6 | 96.8 | 93.1 |
| 5 | 5 | PNAVCETDKWKYENPC | B5R | PNAVCETDKWKYENPC | 98.6 | 93.6 | 96.8 | 93.1 |
| 6 | 6 | CYILHSDYQLFSDAKA | A33R | CYIFHSDYQLFSDAKA (SEQ ID NO: 39) | 99.3 | 94 | 96.5 | 95 |
| 7 | 7 | AKLTSTETSFNNNQKV | B5R | AKLTSTETSFNDKQKV (SEQ ID NO: 40) | 98.6 | 93.6 | 96.8 | 93.1 |
| 8 | 8 | CETDKWKYENPCKKMC | B5R | CETDKWKYENPCKKMC | 98.6 | 93.6 | 96.8 | 93.1 |
| 9 | 9 | TVYGDKIQGKNKRKRV | A33R | TVYGDKIQGKNKRKRV | 99.3 | 94 | 96.5 | 95 |
| 10 | 10 | KITNVTTKFEQIEKCC | A27L | KITNVTTKFEQIEKCC | 99.5 | 98.1 | 94.6 | 97.3 |
| 11 | 11 | AFLIVRLNQCMSANEA | A33R | AFLIVRLNQCMSANEA | 99.3 | 94 | 96.5 | 95 |
| 12 | 12 | SSTTQYDHKESCNGLY | A33R | SSTTQYKHQESCNGLY (SEQ ID NO: 41) | 99.3 | 94 | 96.5 | 95 |
| 13 | 13 | SGSTFSIGGVIHLSCK | B5R | SGSTFSIGGVIHLSCK | 98.6 | 93.6 | 96.8 | 93.1 |
| 14 | 14 | CNLTVKNMCSADADAQ | L1R | CNLTVKNMCSADADAQ | 100 | 99.6 | 98.8 | 98.4 |
| 15 | 15 | NCAIKALMQLTTKATT | L1R | NCAIKALMQLTTKATT | 100 | 99.6 | 98.8 | 98.4 |
| 16 | 16 | KCDIEIGNFYIRQNHG | L1R | KCDIEIGNFYIRQNHG | 100 | 99.6 | 98.8 | 98.4 |
| 17 | 17 | QNVIIDECYGAPGSPT | L1R | QNVIIDECYGAPGSPT | 100 | 99.6 | 98.8 | 98.4 |

TABLE 1-continued

Characteristics of identified MHC II-restricted T helper epitopes.

| SEQ ID NO: | Poly-peptide #[a] | Sequence[b] | Protein[c] | VARV sequence[d] | Protein sequence homology[e] | | | |
|---|---|---|---|---|---|---|---|---|
| | | | | | VACV | VARV | MPXV | CMLV |
| 18 | 18 | GVIFLISVIVLVCSCD | B5R | GVIFLISVIVLVCSCN (SEQ ID NO: 42) | 98.6 | 93.6 | 96.8 | 93.1 |
| 19 | 19 | AALFMYYAKRMLFTST | L1R | AALFMYYAKRMLFTST | 100 | 99.6 | 98.8 | 98.4 |

[a]An arbitrarily assigned number, used to identify polypeptides discussed in the text.
[b]Sequence of the identified epitope. The VACV-ACAM2000 sequence was used for peptide library synthesis.
[c]Vaccinia protein name following VACV-Copenhagen designation.
[d]Consensus variola sequence with differences indicated by bold, underlined font.
[e]Average sequence homology between the protein listed in column c and the homologs from the indicated poxviruses (VACV = vaccinia, VARV = variola, MXPX = monkeypox, CMLV = camelpox). The VACV-ACAM2000 protein sequences were compared to sequence from each strain of the indicated poxvirus strains available from the Poxvirus Bioinformatics Resource Center (www.poxvirus.org). The average homology for each poxvirus was then calculated and presented in this table.

TABLE 2

Characteristics of newly identified T cell epitopes.

| SEQ ID NO: | Poly-peptide #[a] | Sequence[b] | Protein[c] | VARV sequence[d] | Protein sequence homology[e] | | | |
|---|---|---|---|---|---|---|---|---|
| | | | | | VACV | VARV | MPXV | CMLV |
| 20 | 20 | IRISMVISLLSMITMS | A33R | IRISMVISLLSMITMS | 99.3 | 94 | 96.5 | 95 |
| 21 | 21 | EVLFRLENHAETLRAA | A27L | DVLFRLENHAETLRAA (SEQ ID NO: 43) | 99.5 | 98.1 | 94.6 | 97.3 |
| 22 | 22 | EQTSVFSATVYGDKIQ | A33R | EQTSVFSATVYGDKIQ | 99.3 | 94 | 96.5 | 95 |
| 23 | 23 | DKIQGKNKRKRVIGLC | A33R | DKIQGKNKRKRVIGIC (SEQ ID NO: 44) | 99.3 | 94 | 96.5 | 95 |
| 24 | 24 | FSIGGVIHLSCKSGFI | B5R | FSIGGVIHLSCKSGFI | 98.6 | 93.6 | 96.8 | 93.1 |
| 25 | 25 | KLEQEANASAQTKCDI | L1R | KLEQEANASAQTKCDI | 100 | 99.6 | 98.8 | 98.4 |
| 26 | 26 | ITINCDVGYEVIGASY | B5R | ITINCDVGYEVIGASY | 98.6 | 93.6 | 96.8 | 93.1 |
| 27 | 27 | IIVALTIMGVIFLISV | B5R | IIVALTIMGVIFLISV | 98.6 | 93.6 | 96.8 | 93.1 |
| 28 | 28 | KATTQIAPRQVAGTGV | L1R | KATTQIAPRQVAGTGV | 100 | 99.6 | 98.8 | 98.4 |
| 29 | 29 | MYYAKRMLFTSTNDKI | L1R | MYYAKRMLFTSTNDKI | 100 | 99.6 | 98.8 | 98.4 |
| 30 | 30 | DTFFRTSPMVIATTDM | L1R | DTFFRTSPMVIATTDI (SEQ ID NO: 45) | 100 | 99.6 | 98.8 | 98.4 |
| 31 | 31 | QIAPRQVAGTGVQFYM | L1R | QIAPRQVAGTGVQFYM | 100 | 99.6 | 98.8 | 98.4 |
| 32 | 32 | KRMLFTSTNDKIKLIL | L1R | KRMLFTSTNDKIKLIL | 100 | 99.6 | 98.8 | 98.4 |
| 33 | 33 | ANKENVHWTTYMDTFF | L1R | ANKENVHWTTYMDTFF | 100 | 99.6 | 98.8 | 98.4 |
| 34 | 34 | VIILAALFMYYAKRML | L1R | VIILAALFMYYAKRML | 100 | 99.6 | 98.8 | 98.4 |
| 35 | 35 | NVHWTTYMDTFFRTSP | L1R | NVHWTTYMDTFFRTSP | 100 | 99.6 | 98.8 | 98.4 |
| 36 | 36 | TTYMDTFFRTSPMVIA | L1R | TTYMDTFFRTSPMVIA | 100 | 99.6 | 98.8 | 98.4 |

Polypeptides listed in this table elicited significant IFNγ ELISPOT responses with total PBMCs and may represent CD4 and/or CD8 epitopes. Please refer to Table 1 for a description of each column Table 1 shows peptides recognized by CD4+ T cells that are presumably presented by HLA class II molecules. Table 2 shows peptides recognized by PBMCs. These epitopes were not definitively linked to CD4+ T cell responses due to either a lack of sufficient cells to test the CD4+ T cell responses, or more commonly, the disappearance of responses to individual peptides when CD8+ T cells were removed from the ELISPOT assays. These results indicate that the polypeptides listed in Table 2 are likely presented by HLA class I molecules to CD8+ T cells. In support of this hypothesis, the sequence VLFRLENHA within peptide #21 (Table 2) has been identified as an HLA-A*0201 epitope (Otero et al., *Vaccine*, 24(21):4461-4470 (2006)), as has the sequence QTSVFSATV within peptide #22 (Sidney et al., *Immunome Res.*, 4:2 (2008)). The results do not rule out the possible presence of HLA II epitopes eliciting minor responses below the level of sensitivity of the assays. For example, various DR binding epitopes within peptides #23 and #24 have been identified (Sirven et al., *Mol. Immunol.*, 46(7):1481-1487 (2009)). In some cases, the first round peptide pool screening was immediately followed by individual peptide testing in CD8 T cell depleted PBMCs. Of the 36 peptides listed in Table 1 and Table 2, only three were recognized by more than 1 individual. Peptide #6 was recognized by 3 subjects, and peptides #15 and #20 were recognized by two individuals.

Figure 5A:
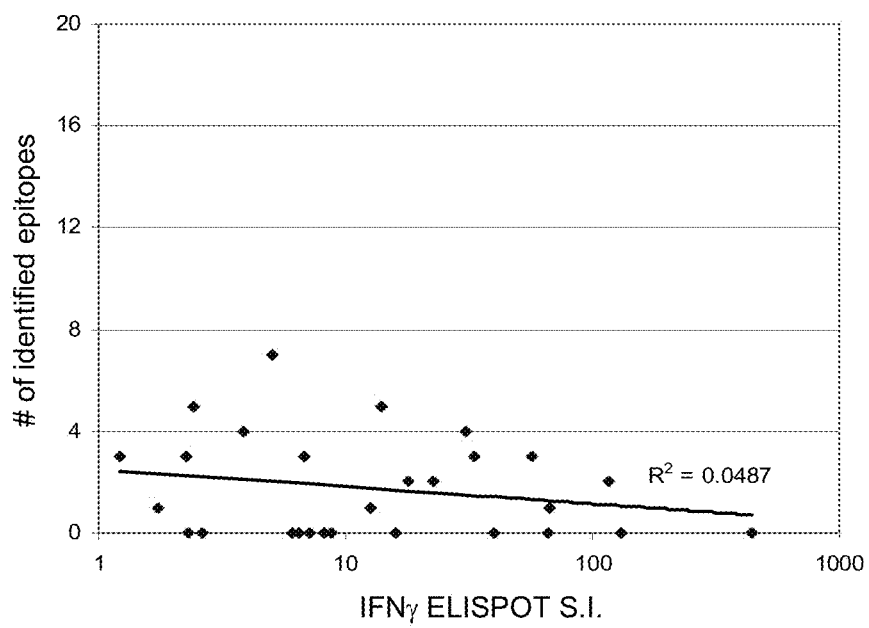
FIG. 5A is a scatter plot plotting a correlation between immune responses and the number of identified epitopes. Vaccinia-specific IFNγ ELISPOT S.I. is presented on the X-axis, and the number of identified epitopes is presented on the Y-axis. The best fit line is depicted in gray with the $r^2$ value indicated on the graph. Each diamond represents a single subject's response.
Figure 5B:
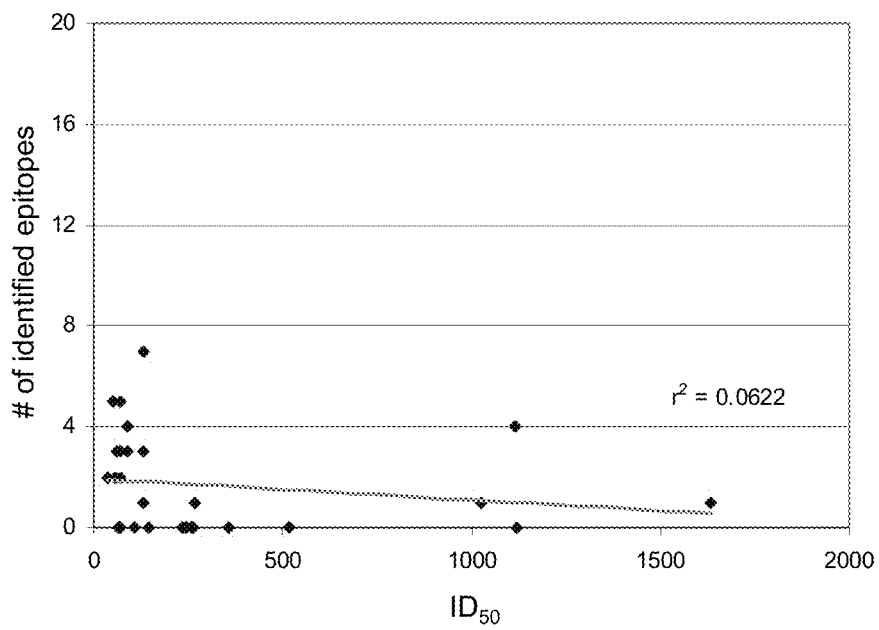
FIG. 5B is a scatter plot plotting a correlation between immune responses and the number of identified epitopes. The vaccinia-specific neutralizing antibody $ID_{50}$ is presented on the X-axis, and the number of identified epitopes is presented on the Y-axis. The best fit line is depicted in gray with the $r^2$ value indicated on the graph. Each diamond represents a single subject's response.
Figure 6A:
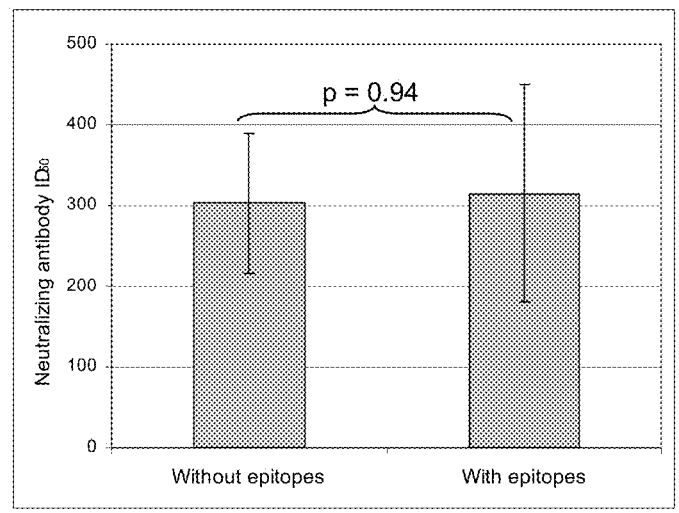
FIG. 6A is a bar graph plotting a comparison of immune responses (humoral response represented by $ID_{50}$ values) in subjects with and without identified epitopes.
Figure 6B:
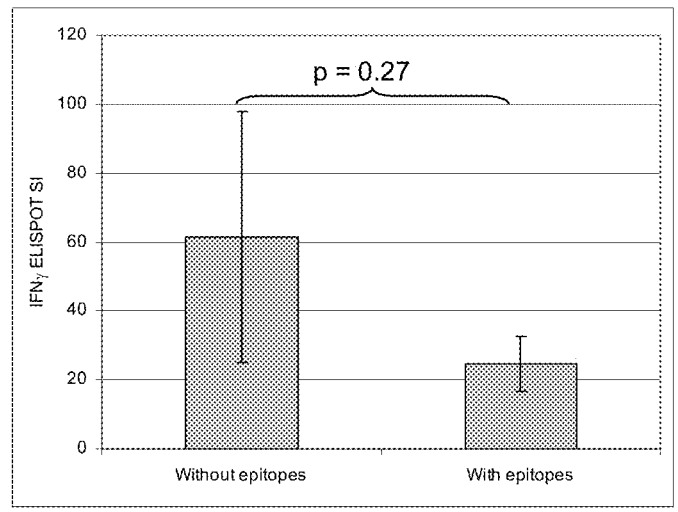
FIG. 6B is a bar graph plotting a comparison of immune responses (cellular immunity denoted by IFNγ ELISPOT S.I.) in subjects with and without identified epitopes. Average immune responses to vaccinia virus (humoral response represented by $ID_{50}$ values and cellular immunity denoted by IFNγ ELISPOT S.I.) for subjects with identified T cell epitopes were compared to the anti-viral immune responses of subjects for which no epitopes were found. Student's t test comparison p-values are indicated on each graph.

Epitope identification did not show any correlation with the magnitude of either humoral or cellular vaccinia-specific responses (FIG. 5), nor were there significant differences in immune response between individuals with identified peptide responses and those without (FIG. 6).

The results support the hypothesis that proteins targeted by B cell responses are likely to also contain T helper epitopes, as multiple peptides from each of the four target proteins have been identified.

Epitope Characterization

As shown in Table 1, the identified vaccinia polypeptides exhibited remarkable sequence homology (>97%) with their variola counterparts. In fact, 27 of the 36 polypeptides were 100% conserved, of the 9 polypeptides with different protein sequences (Proteins #1, #4, #6, #7, #12, #18, #21, #23 and #30 from Table 1 and Table 2). Six polypeptides differed by only a single amino acid. Two polypeptides had two amino acid differences, and one polypeptide had 5 divergent amino acids. At the protein level, these four proteins exhibited very high homology between vaccinia, variola, monkeypox, and camelpox viruses.

Several of the VARV homologs of the polypeptides in Table 1 and Table 2 were synthesized, and an IFNγ response to the VARV version of polypeptide #18 but not to the polypeptides #1, #4, #6, #21, or #30 (Table 3) was detected.

TABLE 3

Comparison of immune reactivity to VACV and VARV homologs.

| Polypeptide #[a] | Sequence[b] | Virus[c] | S.I.[d] | p-value[e] |
|---|---|---|---|---|
| 1 | KADEDDNEETLKQRLT | VACV | 1.5 | 0.01 |
| | KADGDDNEETLKQRLT | VARV | 1 | 0.68 |
| 4 | LYNKPLYEVNSTMTLS | VACV | 1.5 | 0.01 |
| | LYNKPLYEVNAIITLI | VARV | 1 | 0.92 |
| 6 | CYILHSDYQLFSDAKA | VACV | 3.5 | 0.006 |
| | CYIFHSDYQLFSDAKA | VARV | 1.1 | 0.95 |
| 18 | GVIFLISVIVLVCSCD | VACV | 2.1 | 0.012 |
| | GVIFLISVIVLVCSCN | VARV | 2.3 | 0.02 |
| 21 | EVLFRLENHAETLRAA | VACV | 2.5 | 0.04 |
| | DVLFRLENHAETLRAA | VARV | 0.7 | 0.16 |
| 30 | DTFFRTSPMVIATTDM | VACV | 2 | 0.008 |
| | DTFFRTSPMVIATTDI | VARV | 1.1 | 0.89 |

[a]Polypeptides number from Tables 1 and 2.
[b]Polypeptide sequence.
[c]Virus containing the listed polypeptide sequence.
[d]Stimulation index (mean spots per well containing polypeptide/mean spots per background wells).
[e]p-Value comparing spots per well with polypeptide vs. spots per well with DMSO control. Positive responses are in bold font and represent peptides with a 1.5 fold increase in mean spots/well over background (S.I. ≥ 1.5) and a p-value of ≤0.05.

There were not any clearly immunodominant polypeptides identified as most of the polypeptides were recognized by a single individual. In fact, of the 36 epitopes identified, only three were recognized by more than one individual. At the protein level, more epitopes from the B5R (11 epitopes) and L1R (15 epitopes) proteins were identified than the A33R (7 epitopes) or A27L (3 epitopes) proteins.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inducing an immune response against at least one isolated polypeptide, wherein the sequence of said polypeptide consists of the sequence as set forth in any one of SEQ ID NOs:1-19, wherein said method comprises administering said polypeptide to a subject in an amount effective to induce an immune response against said polypeptide.

2. The method of claim 1, wherein said polypeptide is administered in combination with at least one HLA class-I restricted vaccinia virus derived polypeptide.

3. The method of claim 1, wherein said polypeptide is administered in combination with at least one additional polypeptide, wherein the sequence of said additional polypeptide consists of the sequence as set forth in any one of SEQ ID NOs:20-36.

4. The method of claim 1, wherein said polypeptide is administered in combination with a pharmaceutically acceptable excipient, carrier, diluent, or vehicle.

5. The method of claim 1, wherein said immune response is a cell mediated immune response.

* * * * *